United States Patent
Marsh et al.

(10) Patent No.: US 11,498,735 B2
(45) Date of Patent: *Nov. 15, 2022

(54) ARRAY OF WET WIPE PACKAGES

(71) Applicant: The Procter & Gamble Company, Cincinnati, OH (US)

(72) Inventors: Randall Glenn Marsh, Hamilton, OH (US); Karolin K. Kroening, Lawrenceburg, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/373,829

(22) Filed: Jul. 13, 2021

(65) Prior Publication Data
US 2021/0339931 A1 Nov. 4, 2021

Related U.S. Application Data

(63) Continuation of application No. 15/892,529, filed on Feb. 9, 2018, now Pat. No. 11,097,881.

(51) Int. Cl.
| | |
|---|---|
| B65D 75/54 | (2006.01) |
| A61K 8/02 | (2006.01) |
| A61Q 19/10 | (2006.01) |
| A61K 8/368 | (2006.01) |
| D21H 27/00 | (2006.01) |
| A61K 8/36 | (2006.01) |
| D21H 11/12 | (2006.01) |
| C11D 3/50 | (2006.01) |
| C11D 17/04 | (2006.01) |
| C11D 3/37 | (2006.01) |
| A61Q 19/00 | (2006.01) |
| B65D 83/08 | (2006.01) |
| C11D 3/48 | (2006.01) |
| D21H 11/00 | (2006.01) |
| A47K 10/32 | (2006.01) |
| D21H 13/14 | (2006.01) |

(52) U.S. Cl.
CPC ............ *B65D 75/54* (2013.01); *A61K 8/0208* (2013.01); *A61K 8/36* (2013.01); *A61K 8/368* (2013.01); *A61Q 19/007* (2013.01); *A61Q 19/10* (2013.01); *B65D 83/08* (2013.01); *C11D 3/3757* (2013.01); *C11D 3/50* (2013.01); *C11D 17/049* (2013.01); *D21H 11/12* (2013.01); *D21H 27/002* (2013.01); *A47K 2010/3266* (2013.01); *A61K 2800/884* (2013.01); *B32B 2262/067* (2013.01); *B32B 2262/14* (2013.01); *C11D 3/48* (2013.01); *D21H 11/00* (2013.01); *D21H 13/14* (2013.01)

(58) Field of Classification Search
CPC ........ A61K 8/368; A61K 8/85; A61K 8/9789; A61K 8/0208; A61K 2800/30; A61K 8/362; A61K 2800/524; B65D 25/205; A61Q 19/10

See application file for complete search history.

(56) References Cited

FOREIGN PATENT DOCUMENTS

EP 1614790 A1 1/2006

*Primary Examiner* — Hasan S Ahmed
(74) *Attorney, Agent, or Firm* — Daniel S. Albrecht

(57) ABSTRACT

Described herein is an array of wet wipe packages displayed via a merchandise display system. The array of wet wipe packages includes a first package, a second package, and a third package. The first package includes a first wet wipe having a first coform nonwoven material and a first lotion. The second package includes a second wet wipe having a second coform nonwoven material and a second lotion. The third package includes a third wet wipe having a third coform nonwoven material and a third lotion. The third lotion is different than the first lotion and the second lotion. The first coform nonwoven material, the second coform nonwoven material, and/or the third coform nonwoven material has from about 14.5% to about 45% cotton.

20 Claims, No Drawings

ARRAY OF WET WIPE PACKAGES

CROSS-REFERENCE TO RELATED APPLICATIONS

This application is a continuation of U.S. patent application Ser. No. 15/892,529, filed on Feb. 9, 2018, which is incorporated herein by reference in its entirety.

FIELD

Described herein is an array of wet wipe packages, wherein the wet wipe comprises a coform nonwoven material and a lotion, wherein the lotion is resistant to bacteria, mold, and/or yeast growth, and wherein the coform nonwoven material comprises cotton.

BACKGROUND

Wet wipes are constructed from porous or absorbent sheets impregnated with a lotion and they are sold and stored in an air-tight container or wrapper to prevent the sheets drying out. Wet wipes are made for a variety of uses. The two main categories of use are firstly, those for general household cleaning tasks, such as the cleaning of hard surfaces like floors or kitchen surfaces and secondly, those made for personal cleansing, such as the removal of make-up, or the cleaning of infants prior to the fitting of a new diaper or the simple refreshment of the skin after meals or while traveling. Wipes have also found use with feminine health and adult incontinence products.

A major proportion of the wipes intended for the cleansing of human skin are wet wipes which are designed for use with infants and young children. They are particularly used by parents during the changing of babies to clear away any excess fecal or urine residues in the peri-anal region before applying a fresh diaper or nappy. Wet wipes are required to be effective at cleaning while at the same time being very gentle and mild on the skin of the baby. This is especially important given that the skin of the baby around the genitals and anus may become very sensitive or rash-prone after extended contact with urine and fecal matter.

One way to formulate a gentle and mild lotion for a wet wipe is to increase the water content of the lotion. Increasing the water content of the lotion has the added benefit of decreasing the amount of chemicals applied to the skin. However, the higher the water content of a lotion, the more difficult it is to meet preservative system efficacy requirements for microbial growth.

Therefore, there is a need for a wet wipe comprising a gentle, high water content lotion that meets preservative system efficacy requirements for microbial growth. More specifically, there is a need for an array of wet wipe packages comprising a wet wipe comprising cotton and/or a gentle, 99% water lotion that can meet preservative system efficacy requirements for microbial growth.

SUMMARY OF THE INVENTION

Described herein is an array of wet wipe packages displayed via a merchandise display system, the array of wet wipe packages comprising (a) a first package comprising a first wet wipe, wherein the first wet wipe comprises a first coform nonwoven material and a first lotion, and wherein the first lotion is devoid of perfume; (b) a second package comprising a second wet wipe, wherein the second wet wipe comprises a second coform nonwoven material and a second lotion, wherein the second lotion comprises a perfume; and (c) a third package comprising a third wet wipe, wherein the third wet wipe comprises a third coform nonwoven material and a third lotion, wherein the third lotion is different than the first lotion and the second lotion; wherein the first coform nonwoven material, the second coform nonwoven material, and/or the third coform nonwoven material comprise from about 14.5% to about 45% cotton by weight of the second coform nonwoven material, and/or the third coform nonwoven material; and wherein the first coform nonwoven material, the second coform nonwoven material, and/or the third coform nonwoven material comprise a matrix of a synthetic fiber, cellulosic fiber, and cotton fiber.

Also described herein is an array of wet wipe packages displayed via a merchandise display system, the array comprising (a) a first package comprising a first wet wipe, wherein the first wet wipe comprises a first coform nonwoven material and a first lotion, wherein the first lotion comprises aloe barbadensis leaf juice and tocopheryl acetate, and wherein the first lotion is devoid of fragrance and/or perfume; (b) a second package comprising a second wet wipe, wherein the second wet wipe comprises a second coform nonwoven material and a second lotion, wherein the second lotion comprises *Cucumis sativus* fruit extract, glycerin, and a perfume; (c) a third package comprising a third wet wipe, wherein the third wet wipe comprises a third coform nonwoven material and a third lotion, wherein the third lotion comprises coco-betaine, and wherein the third lotion is devoid of glycerin; and (d) a fourth package comprising a fourth wet wipe, wherein the fourth wet wipe comprises a fourth coform nonwoven material and a fourth lotion, wherein the fourth coform nonwoven material comprises from about 14.5% to about 45% cotton by weight of the fourth coform nonwoven material, wherein the fourth lotion comprises from about 98.5% to about 99.5% water by weight of the fourth lotion, and wherein the fourth lotion is devoid of fragrance and/or perfume.

Also described herein is an array of wet wipe packages displayed via a merchandise display system, the array comprising (a) a first package comprising a first wet wipe, wherein the first wet wipe comprises a first coform nonwoven material and a first lotion, wherein the first coform nonwoven material comprises from about 14.5% to about 45% cotton by weight of the first coform nonwoven material, wherein the first lotion comprises aloe barbadensis leaf juice, tocopheryl acetate, and from about 98.5% to about 99.5% water by weight of the first lotion, wherein the first lotion is devoid of fragrance and/or perfume, wherein the first package comprises one or more communications that the first coform nonwoven material comprises cotton, and wherein the first package comprises one or more communications that the first lotion comprises 99% water; (b) a second package comprising a second wet wipe, wherein the second wet wipe comprises a second coform nonwoven material and a second lotion, wherein the second lotion comprises *Cucumis sativus* fruit extract, glycerin, and a perfume; and (c) a third package comprising a third wet wipe, wherein the third wet wipe comprises a third coform nonwoven material and a third lotion, wherein the third lotion comprises coco-betaine, and wherein the third lotion is devoid of glycerin.

DETAILED DESCRIPTION

The following definitions may be useful in understanding the present disclosure:

"Devoid of," "free of," and the like, as those terms are used herein, means that the wet wipe, lotion, and/or substrate does not have more than trace amounts of background levels of a given material, ingredient, or characteristic following these qualifiers; the amount of the material or ingredient does not cause harm or irritation that consumers typically associate with the material or ingredient; or the material or ingredient was not added to the wet wipe, lotion, and/or substrate intentionally. In some instances, "devoid of" and "free of" can mean there is no measurable amount of the material or ingredient. For example, the wet wipe in some forms contains no measurable amounts of chlorine.

"Soil" refers herein to matter that is extraneous to a surface being cleaned. For example, soils include body exudates, household matter, and outdoor matter. Body exudates include feces, menses, urine, vomitus, mucus, and the like. Household matter includes food, beverages, combinations thereof, and the like. Outdoor matter includes dirt, mud, snow, paint, crayons, and the like.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes.

"Substrate" refers herein to a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Wipe" refers herein to a piece of material, generally non-woven material, used in cleansing hard surfaces, food, inanimate objects, toys and body parts. In particular, many currently available wipes may be intended for the cleansing of the perianal area after defecation.

As used herein, percentages are given as the weight of the component to the total weight of the lotion, unless otherwise indicated. Percentages reflect 100% active component material. For example, if a component is available in a dispersion at a concentration of 50% component to dispersion, by weight, twice as much of the dispersion, by weight, would be added to the lotion to provide the equivalent of 100% active component.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

As used herein, the articles "a" and "an" when used herein, for example, "an anionic emulsifier" or "a fiber" is understood to mean one or more of the material that is claimed or described.

Lotion

The wet wipe described herein comprises a lotion. The lotion described herein comprises from about 98% water to about 99.9% water, alternatively from about 98.5% water to about 99.7% water, alternatively from about 98.5% water to about 99.5% water, alternatively from about 99% water to about 99.3% water, by weight of the lotion. At such a high water content, the lotion described herein must comprise a strong preservative system for preventing microbial growth. The percent water in the lotion can be calculated using the Water Content Method provided herein.

The lotion described herein may be incorporated onto a substrate at a load of about 200% to about 600%, alternatively from about 300% to about 500%, and alternatively from about 325% to about 460%, by weight of the substrate.

The lotions described herein, and wipes comprising the lotions, may be made by the conventional processes described in the art. Alternatively, the lotions and wipes are made according to U.S. Pat. No. 7,365,030 entitled "Process for making a wet wipe using a concentrated emulsion" by Sylvie Chamba et al., which is incorporated herein by reference.

Lotion Preservative System

Controlling microbiological growth is a necessary function of wet wipes, especially wet wipes comprising a high water content lotion. To control microbiological growth, the lotion described herein comprises a preservative system. The preservative system may include a preservative enhancing agent and one or more preservatives. A preservative may be understood to be a chemical or natural compound or a combination of compounds reducing the growth of microorganisms, thus enabling a longer shelf life for a package of wet wipes (opened or not opened) as well as creating an environment with reduced growth of microorganisms when transferred to the skin during the wiping process.

The spectrum of activity of the preservative may include bacteria, molds, and/or yeast. Each of such microorganisms may be killed by the preservative. Another mode of action to be contemplated may be the reduction of the growth rate of the microorganisms without active killing. Both actions however result in a drastic reduction of the population of microorganisms.

The lotion described herein comprises a preservative which is an organic acid. The lotion comprises at least 0.055%, alternatively at least 0.06%, alternatively at least 0.07%, alternatively from about 0.05% to about 0.6%, alternatively from about 0.05% to about 0.4%, alternatively from about 0.05% to about 0.3%, alternatively from about 0.055% to about 0.1%, alternatively from about 0.08% to about 0.4%, alternatively from about 0.2% to about 0.3%, alternatively from about 0.06% to about 0.085%, and alternatively from about 0.07% to about 0.084% of the organic acid by weight of the lotion, according to the HPLC test method described herein. The organic acid may be selected from the group consisting of anisic acid, malic acid, lactic acid, dehydroacetic acid, gluconic acid, salicylic acid, benzoic acid, sorbic acid, levulinic acid, and mixtures thereof. Alternatively, the organic acid may be benzoic acid or sorbic acid. Alternatively, the organic acid may be benzoic acid. Salts of organic acids may also be present in the lotion described herein. Exemplary salts of organic acids include sodium benzoate, sodium gluconate, sodium levulinate, sodium anisate, and/or potassium sorbate. The percent organic acid in the lotion can be calculated using the Organic Acid Content Test Methods provided herein.

The organic acids described herein are organic compounds with acidic properties. The most common organic acids are carboxylic acids, whose acidity is associated with a carboxyl group —COOH. In general, organic acids are weak acids that dissociate in an aqueous solution to achieve equilibrium. The percent dissociation can be defined as the ratio of the amount of acid dissociated to the initial concentration of acid, multiplied by 100. The percent dissociation can be calculated based on the pKa of the weak acid and the pH of the aqueous solution. As an example, when sodium benzoate is formulated into an aqueous lotion composition, it forms an equilibrium between sodium benzoate and benzoic acid based on its pKa of 4.2 and on the pH of the aqueous lotion composition. At a pH of 4.2, there is 50% sodium benzoate and 50% benzoic acid in the lotion composition.

Without being bound by theory, it is believed that different organic acids present in a wipe lotion may interact to different degrees with the various kinds of nonwoven fibers that are present in a wipe substrate, once the wipe lotion is impregnated into the substrate and remains there until consumer usage. Different kinds of interactions may occur based on the physical and chemical properties of the organic acid and of the nonwoven fiber. These interactions may lead to absorption of the organic acid to the surface of the fiber or to absorption of the organic acid into the structure of the fiber.

Hansen's solubility parameters are a way of predicting if one material will want to interact with and potentially dissolve in another material. Each molecule is given three Hansen parameters, one for the dispersion forces between molecules, one for the dipolar intermolecular force between molecules, and one hydrogen bonding between molecules. These parameters serves as co-ordinates for a point in three dimensions known as the Hansen space. The nearer two molecules are in this three-dimensional space, the more compatible they are, the more likely they are interact, and the greater the potential for them to dissolve in each other.

In the case of polyester fibers, certain organic acids such as benzoic acid share physical and chemical similarities to polyester that cause them to have a fairly similar Hansen space. This means that, over time, while the wipe lotion is in contact with wipe substrate comprising polyester fibers, certain organic acids such as benzoic acid will interact with and even be absorbed into the polyester fibers, reducing their concentration in the wipe lotion and hence making them unavailable to participate in preservative system efficacy.

The preservative system of the lotion described herein may include additional compounds, for example chelating agents, such as ethylenediamine tetraacetic acid (EDTA) and its salts, diethylene triamine pentaacetic acid (DTPA) and its salts, and/or gluconic acid and its salts. The chelating agent may be disodium EDTA and/or sodium gluconate.

The lotion described herein may be incorporated into a substrate at a load of about 200% to about 600%, alternatively from about 325% to about 460%, by weight of the substrate. The substrate may be a nonwoven material.

The preservative system in the lotion described herein may include one or more preservative enhancing agents. Exemplary preservative enhancing agents include sorbitan caprylate, glyceryl caprylate/caprate, or combinations thereof. An exemplary sorbitan caprylate is manufactured by Clariant under the designation VELSAN® SC. An exemplary glyceryl caprylate/caprate may be CremerCOOR® GC810, CremerCOOR® GCB, or IMWITOR® 742, all available from Peter Cremer, or CAPMUL® 708G, available from Abitec.

The lotion described herein may comprise from about 0.05% to about 0.25%, alternatively from about 0.07% to about 0.22%, alternatively from about 0.09% to about 0.2%, alternatively from about 0.11% to about 0.18%, and alternatively from about 0.14% to about 0.18% of a preservative enhancing agent by weight of the lotion.

Lotion Buffering System

The lotion described herein comprises from about 0.3% to about 1%, alternatively from about 0.4% to about 1%, alternatively from about 0.5% to about 0.85%, and alternatively from about 0.6% to about 0.75% of a pH buffering system, by weight of the lotion, which also may help prevent and/or reduce the growth of bacteria, mold, and/or yeast. The pH buffering system may be a citrate-citric acid buffering system at a pH of less than 5. The pH buffering system may be a citrate-citric acid buffering system at a pH of less than 4. The pH buffering system may be a sodium citrate-citric acid buffering system at a pH of less than 5. The pH buffering system may be a sodium citrate-citric acid buffering system at a pH of less than 4. The pH buffering system may comprise sodium citrate dihydrate and citric acid anhydrous. The lotion described herein may have a pH from about 3.5 to about 7, alternatively from about 3.5 to about 6, alternatively from about 3.6 to about 4.8, alternatively from about 3.6 to about 4.4, alternatively from about 3.6 to about 4.2, and alternatively from about 3.8 to about 4.2.

The lotion described herein may have an Equivalence Value from about 25 to about 100, alternatively from about 30 to about 95, alternatively from about 55 to about 90, alternatively from about 65 to about 90, alternatively from about 60 to about 80, alternatively from about 62 to about 75, and alternatively from about 65 to about 70, according to the Buffering Capacity Test Method described herein.

A lotion having a higher Equivalence Value, such as from about 65 to about 90, may be desired because it can help to protect a baby's skin against irritation caused by feces and urine residue that can remain after cleaning. The proteases in feces that damage the skin can start to become active around pH 5 and can reach peak activity between pH 7 to 8. Urea in urine may be converted to ammonia by bacteria on the skin, elevating the pH and making the fecal proteases more active. By depositing a lotion with a higher Equivalence Value on the skin, an acidic buffer may be created that resists the climb in pH that would normally occur over time when trace amounts of feces and urine are present. By resisting the climb in pH, a lotion with a higher Equivalence Value can protect the skin from damage caused by fecal proteases and reduce the likelihood that rash will occur between diaper changes.

The lotion described herein may be devoid of phenoxyethanol.

Lotion Optional Ingredients

The lotion described herein may include various optional ingredients, such as surfactants, emollients, colorants, opacifying agents, film-formers, soothing agents, skin protectants, medically active ingredients, healing actives, and the like, such as described in U.S. Pat. Nos. 7,666,827; 7,005,557; 8,221,774; and U.S. Patent Application Publication No. 2011/0268777.

The lotion described herein may comprise an emollient. Emollients may (1) hydrate soil residues (for example, fecal residues or dried urine residues or menses residues), thus enhancing their removal from the skin, (2) hydrate the skin, thus reducing its dryness and irritation, (3) protect the skin from later irritation (for example, caused by the friction of an absorbent article) as the emollient is deposited onto the skin and remains at its surface as a thin protective layer, and (4) provide a desired sensory feel to the lotion and/or the skin.

The emollient may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

The lotion described herein may comprise a mixture of caprylic/capric triglycerides in combination with Bis-PEG/PPG-16/16 PEG/PPG-16/16 dimethicone known as ABIL® CARE 85, available from Evonik Industries.

The lotion described herein may include one or more surfactants. The surfactant may be an individual surfactant or a mixture of surfactants. The surfactant may be a polymeric surfactant or a non-polymeric one. The surfactant or combinations of surfactants may be mild, which means that the surfactants provide sufficient cleaning or detersive benefits but do not overly dry or otherwise harm or damage the skin. The surfactant, when present in the lotion, may be present in an amount ranging from about 0.05% to about 1%, alternatively from about 0.075% to about 0.5%, alternatively from about 0.1% to about 0.2%, and alternatively from about 0.15% to about 0.2% by weight of the lotion.

The surfactant may comprise PEG-40 Hydrogenated Castor Oil (PEG-40 HCO), such as EMULSOGEN® HCW049 manufactured by Clariant. The surfactant may comprise a polyglyceryl ester or a mixture of polyglyceryl esters.

The lotion described herein may comprise one or more rheology modifiers. A rheology modifier may help to stabilize the lotion by reducing or preventing coalescence of droplets of the hydrophobic materials in the composition.

Non-limiting examples of rheology modifiers include, but are not limited to, hydrocolloids, including natural gums, such as xanthan gum. The lotion described herein may comprise from about 0.01% to about 0.1%, alternatively from about 0.03 to about 0.08%, alternatively from about 0.05% to about 0.07%, and alternatively about 0.06% of a rheology modifier by weight of the lotion.

The wet wipe and/or lotion described herein may be devoid of fragrance and/or perfume.

The lotion described herein may comprise other ingredients selected from the group consisting of malic acid, aloe barbadensis leaf juice, tocopheryl acetate, coco-glucoside, caprylyl glycol, *Cucumis sativus* (cucumber) fruit abstract, *Camellia sinensis* (green tea) leaf extract, and/or *Calendula officinalis* flower extract, *Cocos nucifera* (coconut) oil, and combinations thereof, at levels from amount 0.0001% to about 5%, alternatively from about 0.001% to about 3%, alternatively from about 0.01% to about 1%, alternatively from about 0.05% to about 0.8%, and alternatively from about 0.1% to about 0.5%, by weight of the lotion.

Wet Wipe Substrate

The lotion described herein may be loaded onto a substrate to form a wet wipe. The substrate may be a nonwoven material. The nonwoven material may comprise one or more layers of fibrous structures, wherein each layer may include continuous fibers, coextruded fibers, non-continuous fibers, and combinations thereof.

The substrate described herein comprises from about 5% to about 100%, alternatively from about 15% to about 95%, alternatively from about 25% to about 90%, alternatively from about 35% to about 90%, alternatively from about 45% to about 85%, alternatively from about 50% to about 80%, alternatively from about 55% to about 75%, alternatively from about 65% to about 75% polyester, by weight of the substrate. The polyester may comprise less than 100 ppm antimony or the polyester may be devoid of antimony.

The substrate described herein comprises from about 14.5% to about 100%, alternatively from about 14.5% to about 95%, alternatively from about 14.5% to about 75%, alternatively from about 14.5% to about 45%, alternatively from about 15% to about 40%, alternatively from about 15% to about 25%, alternatively from about 0.1% to about 10%, and alternatively from about 15% to about 20% cotton, by weight of the substrate. The cotton may be devoid of chlorine. The cotton may be organic cotton. The cotton may not be bleached. The cotton may be free or substantially free of visual foreign matter, including cotton leaves, stalk, and/or other plant matter that has not been fully removed from the cotton fiber. The average visual foreign matter (VFM)<9 mm2 per linear meter of the substrate may be from about 0.001 VFM to about 0.05 VFM, alternatively from about 0.005 VFM to about 0.03 VFM, alternatively from about 0.007 VFM to about 0.02 VFM, and alternatively from about 0.009 VFM to about 0.015 VFM, when the width of the substrate is 3 meters, using a web inspection vision system which may be available from Cognex.

The substrate described herein may comprise from about 5% to about 50%, alternatively from about 10% to about 30%, alternatively from about 5% to about 25%, alternatively from about 10% to about 20%, and alternatively about 15% viscose, by weight of the substrate.

The substrate described herein may comprise from about 14.5% to about 20% cotton by weight of the substrate, from about 10% to about 20% viscose by weight of the substrate, and from about 60% to about 80% polyester by weight of the substrate.

Any additional fibers of the substrate may be comprised of any natural, cellulosic, and/or wholly synthetic material. The substrate may comprise from about 5% to about 85%, alternatively from about 10% to about 65%, alternatively from about 15% to about 45%, alternatively from about 20 to about 35%, alternatively from about 0.1% to about 30%, alternatively from about 0.5% to about 5%, and alternatively from about 0.01% to about 1% of the additional fibers, by weight of the substrate. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include wood pulp, typical northern softwood Kraft, typical southern softwood Kraft, typical CTMP, typical deinked, corn pulp, acacia, eucalyptus, aspen, reed pulp, birch, maple, radiata pine and combinations thereof. Other sources of natural fibers from plants include albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they may be found in nature. Mechanical and/or chemical manipulation of natural fibers does not exclude them from what are considered natural fibers with respect to the development described herein.

The synthetic fibers may be any material, such as those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. Further, the synthetic fibers may be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bicomponent fibers may be used as a component fiber of the structure, and/or they may be present to act as a binder for the other fibers present in the fibrous structure. Any or all of the synthetic fibers may be treated before, during, or after manufacture to change any desired properties of the fibers. The substrate may comprise hydrophilic fibers, hydrophobic fibers, or a combination thereof.

The substrate may comprise various percentages of natural and/or synthetic fibers. For example, the substrate may comprise 100% synthetic fibers. The substrate may comprise natural and synthetic fibers. For example, the substrate may comprise from about 0% to about 95% natural fibers, with the balance comprising synthetic fibers.

It may be desirable to have particular combinations of fibers to provide desired characteristics. For example, it may be desirable to have fibers of certain lengths, widths, coarseness or other characteristics combined in certain layers, or separate from each other. The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

The fibers may be circular in cross-section, dog-bone shape, delta (i.e., triangular cross section), trilobal, ribbon, or other shapes typically produced as staple fibers. Likewise, the fibers may be conjugate fibers such as bicomponent fibers. The fibers may be crimped and may have a finish, such as a lubricant, applied.

The substrate materials may also be treated to improve the softness and texture thereof. The substrate may be subjected to various treatments, such as physical treatment, hydromolding, hydro-embossing, and ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383,431; stretch aperturing, as described in U.S. Pat. Nos. 5,628,097; 5,658,639; and 5,916,661; differential elongation, as described in U.S. Pat. No. 7,037,569, and other solid state formation technologies as described in U.S. Pat. Nos. 7,553,532 and 7,410,683; zone activation, and the like; chemical treatment, such as rendering part or all of the substrate hydrophobic, and/or hydrophilic, and the like; thermal treatment, such as thermal-embossing, softening of fibers by heating, thermal bonding and the like; and combinations thereof.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other.

The substrate may have a basis weight between about 15, 30, 40, or 45 grams/m$^2$ and about 65, 75, 85, 95, or 100 grams/m$^2$. Exemplary nonwoven substrates are described in U.S. Patent Publication 2012/066852 and U.S. Patent Publication U.S. 2011/244199.

The surface of the substrate may be essentially flat. The surface of the substrate may optionally contain raised and/or lowered portions. The raised and/or lowered portions may be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern of some form.

The substrate may be biodegradable. For example, the substrate could be made from a biodegradable material such as a polyesteramide, or a high wet strength cellulose. The substrate may be dispersible.

The wet wipes described herein may have different properties on different sides of the wet wipe. For example, one side of the wipe may have good cleaning performance and the other side of the wet wipe may have good tactile sensation to the user. In another example, one side of the wet wipe may have an increased cleaning performance as compared to the other side of the wet wipe.

Non-limiting examples of processes for making fibrous structure of the substrate described herein include known wet-laid papermaking processes, air-laid papermaking processes including carded and/or spunlaced processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

The fibrous structures of the substrate described herein may be homogeneous or may be layered. If layered, the substrate may comprise at least two and/or at least three and/or at least four and/or at least five layers.

The fibrous structure of the substrate described herein may be a coform nonwoven material.

"Coform nonwoven material," as used herein, means that the nonwoven material comprises a mixture of at least two different materials wherein at least one of the materials comprises a filament, such as a polypropylene filament, and at least one other material, different from the first material, comprises a solid additive, such as a fiber and/or a particulate. In one example, a coform nonwoven material comprises solid additives, such as fibers, such as wood pulp fibers and/or absorbent gel materials and/or filler particles and/or particulate spot bonding powders and/or clays, and filaments, such as polypropylene filaments. The coform nonwoven material can be a composite of a matrix of meltblown fibers and an absorbent material (e.g., pulp fibers). The coform nonwoven material can also be made according to U.S. Pat. No. 9,260,808 entitled "Flexible coform nonwoven web" by Michael A. Schmidt et al., which is incorporated herein by reference.

"Solid additive" as used herein means a fiber and/or a particulate.

"Particulate" as used herein means a granular substance or powder.

"Fiber" and/or "Filament" as used herein means an elongate particulate having an apparent length greatly exceeding its apparent width, i.e. a length to diameter ratio of at least about 10. For purposes of the present disclosure, a "fiber" is an elongate particulate as described above that exhibits a length of less than 5.08 cm (2 in.) and a "filament" is an elongate particulate as described above that exhibits a length of greater than or equal to 5.08 cm (2 in.).

The substrate described herein may be subjected to any post-processing operations such as embossing operations, printing operations, tuft-generating operations, thermal bonding operations, ultrasonic bonding operations, perforating operations, surface treatment operations such as application of lotions, silicones and/or other materials, folding, and combinations thereof.

Wet Wipe Odor Management Material

The wet wipe described herein may employ an odor management material. The odor management material may be a naturally derived odor management material. The naturally derived odor management material may manage odors inherit to the raw materials used in the manufacture of the wet wipe and/or manage odors associated with wet wipe (e.g., urine, feces, etc). The naturally derived odor management material may include plant extracts and/or odor adsorbing materials such as silicas and zeolites. Exemplary plant extracts may include Extrapone Marigold GW and/or Extrapone Magnolia GW from Symrise Incorporation. The naturally derived odor management material may be substantially scent-free.

Article of Commerce

An article of commerce may comprise a package and a plurality of the wet wipes described herein.

The package may comprise one or more communications that the wet wipe and/or the substrate described herein comprises cotton and/or is devoid of chlorine. The package may comprise a seal of cotton trademarked logo. The package may comprise one or more communications that the wet wipe and/or the lotion described herein is devoid of fragrance and/or perfume. The package may comprise one or more communications that the wet wipe and/or the lotion described herein comprises 99% water. The package may comprise one or more communications that the wet wipe and/or the substrate described herein is devoid of phthalate. The package may comprise one or more communications that the wet wipe and/or the lotion described herein is devoid of alcohol and/or comprises a plant extract. The package may comprise one or more communications that the wet wipe and/or lotion described herein is hypoallergenic. The package may comprise one or more communications that the wet wipe and/or lotion described herein is devoid of phenoxyethanol. The package may comprise one or more communications that the wet wipe and/or lotion described herein is "natural" or "all natural."

The package may be in the form of a container. Containers may include, but are not limited to, PET tubs, flow wrap pouches, individual sachets, chained sachets comprising a tear line between each sachet, and other forms known in the art as suitable for storing nonwoven articles. Additionally, the container may also be manufactured to facilitate removal of individual wet wipes.

The container may be made of any suitable material or materials and may be manufactured in any suitable manner. For example, the container may be made of polystyrene, polypropylene, PET, POET, polyethylene, polyester, polyvinyl alcohol, or the like. The containers may also be made of a mixture of the above materials. The container may be made of a metal foil. The containers may be manufactured by, for example, a vacuum molding process or an injection molding process, or any suitable process.

Additional information on containers, as well as additional optional components for containers, including, but not limited to: container bodies, lids, container features, such as, but not limited to, attachment of lids, hinges, zippers, securing aids, and the like, may be found in U.S. Pat. Nos. Des. 451,279; Des. 437,686; Des. 443,508; Des 443,451; Des 421,901; Des 421,902; Des 416,794; Des 414,637; Des 445,329; 3,982,659; 3,967,756; 3,986,479; 3,994,417; 6,269,970; 5,785,179; 5,366,104; 5,322,178; 5,050,737; 4,971,220; 6,296,144; 6,315,114; 4,840,270; 4,471,881; 5,647,506; 6,401,968; 6,269,969; 6,412,634; 5,791,465; 6,092,690; U.S. Patent Application Publication No. 2002/0064323 published on May 30, 2002, issued to Chin; and WO 00/27268 published on May 18, 2000 and assigned to The Procter & Gamble Company; WO 02/14172 published on Feb. 21, 2002 and assigned to The Procter & Gamble Company; and WO 99/55213 published on Nov. 4, 1999 and assigned to The Procter & Gamble Company.

Array of Wet Wipe Packages

Any of the wet wipes and lotions described herein may be combined to create an array of wet wipe packages. The array of wet wipe packages may be displayed via a merchandise display system and/or may be available to purchase on the internet. The array may comprise two or more distinct but commonly branded (i.e., common brand identifier or common source indicator) wet wipe packages which may be simultaneously offered for sale and presented in a retail setting as an array of available products. The respective wipes packages may be differentiated by their respective labeling information. They may also respectively include other differentiating product features, such as differences in substrate, differences in scent, and/or differences in lotions.

The array of wet wipe packages may comprise a first package, a second package, and a third package. The array of wet wipe packages may comprise a fourth package. The array of wet wipe packages may comprise more than four packages.

The first package may comprise a first wet wipe, wherein the first wet wipe comprises a first coform nonwoven material and a first lotion, and wherein the first lotion is devoid of perfume. The second package may comprise a second wet wipe, wherein the second wet wipe comprises a second coform nonwoven material and a second lotion, wherein the second lotion comprises a perfume. The third package may comprise a third wet wipe, wherein the third wet wipe comprises a third coform nonwoven material and a third lotion, wherein the third lotion is different than the first lotion and the second lotion. At least one of the first lotion, the second lotion, and/or the third lotion has an Equivalence Value from about 30 to about 95.

The first lotion, the second lotion, and/or the third lotion may comprise from about 98.5% to about 99.5% water by weight of the first lotion, the second lotion, and/or the third lotion. The first package, the second package, and/or the third package may comprise one or more communications that the first lotion, the second lotion, and/or the third lotion comprise 99% water.

The first coform nonwoven material, the second coform nonwoven material, and/or the third coform nonwoven material may comprise from about 14.5% to about 45% cotton by weight of the first coform nonwoven material, the second coform nonwoven material, and/or the third coform nonwoven material; and the first coform nonwoven material, the second coform nonwoven material, and/or the third coform nonwoven material may comprise a matrix of a synthetic fiber, cellulosic fiber, and cotton fiber. The cellulosic fiber may be pulp fiber. The cotton fiber may be devoid of chlorine.

At least one of the first wet wipe, the second wet wipe, and the third wet wipe has an MST Yeast & Mold Value at day 28 of from about 3 to about 5, alternatively from about 3.4 to about 4.8, alternatively from about 3.8 to about 5, alternatively from about 3.9 to about 4.7, and alternatively from about 4 to about 4.5, according to the MST Yeast & Mold Value Test Method as described herein.

The first package may comprise one or more communications that the first coform nonwoven material comprises cotton fibers and/or is devoid of chlorine. The first package may also comprise one or more communications that the first lotion is devoid of fragrance and/or perfume. The first package, the second package, and/or the third package may comprise a seal of cotton trademarked logo.

The array may comprise (a) first package comprising a first wet wipe, wherein the first wet wipe comprises a first coform nonwoven material and a first lotion, wherein the first lotion comprises aloe barbadensis leaf juice and tocopheryl acetate, and wherein the first lotion is devoid of fragrance and/or perfume; (b) a second package comprising a second wet wipe, wherein the second wet wipe comprises a second coform nonwoven material and a second lotion, wherein the second lotion comprises *Cucumis sativus* fruit extract, glycerin, and/or a perfume; (c) a third package comprising a third wet wipe, wherein the third wet wipe comprises a third coform nonwoven material and a third lotion, wherein the third lotion comprises coco-betaine, and wherein the third lotion is devoid of glycerin; and (d) a fourth package comprising a fourth wet wipe, wherein the fourth wet wipe comprises a fourth coform nonwoven material and a fourth lotion, wherein the fourth coform nonwoven material comprises from about 14.5% to about 45% cotton by weight of the fourth coform nonwoven material, wherein the fourth lotion comprises from about 98.5% to about 99.5% water by weight of the fourth lotion, and wherein the fourth lotion is devoid of fragrance and/or perfume. The cotton may be devoid of chlorine.

The fourth lotion may comprise an Equivalence Value from about 30 to about 95. The fourth lotion may comprise from about 0.1% to about 0.5% sodium benzoate by weight of the fourth lotion. The fourth lotion may have a pH from about 3.8 to about 4.2.

The fourth package may comprise one or more communications that the fourth coform nonwoven material comprises cotton fibers and/or is devoid of chlorine. The fourth package may comprise one or more communications that the fourth lotion is devoid of fragrance and/or perfume. The fourth package may comprise one or more communications that the fourth lotion comprises 99% water. The fourth package may comprise a seal of cotton trademarked logo.

The array may comprise (a) a first package comprising a first wet wipe, wherein the first wet wipe comprises a first coform nonwoven material and a first lotion, wherein the first coform nonwoven material comprises from about 14.5% to about 45% cotton by weight of the first coform nonwoven material, wherein the first lotion comprises aloe barbadensis leaf juice and/or tocopheryl acetate, and from about 98.5% to about 99.5% water by weight of the first lotion, wherein the first lotion is devoid of fragrance and/or perfume, wherein the first package comprises one or more communications that the first coform nonwoven material comprises cotton, and wherein the first package comprises one or more communications that the first lotion comprises 99% water; (b) a second package comprising a second wet wipe, wherein the second wet wipe comprises a second coform nonwoven material and a second lotion, wherein the second lotion comprises *Cucumis sativus* fruit extract, glycerin, and/or a perfume; and (c) a third package comprising a third wet wipe, wherein the third wet wipe comprises a third coform nonwoven material and a third lotion, wherein the third lotion comprises coco-betaine, and wherein the third lotion is devoid of glycerin.

The first lotion may have an Equivalence Value from about 30 to about 95. The first package may comprise a seal of cotton trademarked logo. The first package may comprise one or more communications that the first coform nonwoven material is devoid of chlorine and/or is devoid of phthalate. The first package may comprise one or more communications that the first lotion is devoid of fragrance and/or perfume.

The array may be displayed on a store shelf, wherein the packages are separate from one another in a way that is visible to a consumer during the consumer's purchasing decision process; wherein the packages are designed to be sold individually; and wherein the packages each comprise a common brand name. The packages may also be sold individually via a website online.

Test Methods

All test methods are carried out in an environment 23±2° C. and 50±5% relative humidity environment unless otherwise specified.

Lotion Expression Method

Lotion is expressed from wet wipes for further analysis using the Lotion Expression Method. In this method, lotion is extracted from one or more like packages of lotioned wipes that have been wetted in a sealed package for at least 28 days at 40° C. and 75% relative humidity in order to collect a desired quantity of lotion for further analysis.

One corner is cut from one sealed wipes package to create a small (approximately 0.25-inch in diameter) hole from which liquid can escape. The package is then positioned between the platens of a uniaxial press with the corner containing the hole for liquid escape hanging outside the edge of the platens such that lotion can be collected in a suitable container as pressure is applied. Pressure is then increasingly applied to the package of wipes and held at 100±10 psi for at least a minute and until no more fluid drains freely from the compressed lotion package, at which point the container holding the collected lotion is sealed tightly until further analysis. This process is repeated until the desired quantity of lotion for further analysis has been collected. If lotion is collected from more than one package of like wipes, all lotion expressed from all like packages is mixed prior to any analysis.

If lotioned wipes are packaged directly in packaging that is not amenable to the pressure/deformation required by this method, lotioned wipes are removed from packaging and are immediately transferred to a rectangular plastic bag and sealed. The rectangular plastic bag is then cut at one corner and placed in the platens of a press and squeezed as specified above.

Water Content Method

In the Water Content Method, a portion of expressed lotion is placed in an oven to facilitate evaporation, and the remaining unevaporated mass is measured. From this, the water content of the starting expressed lotion is calculated.

The Lotion Expression Method is used to express lotion, from which a 5.0±0.1 g aliquot is taken and placed in a 70-mm diameter aluminum weighing boat (such as VWR part number 25433-089, VWR International, Radmor, Pa., USA, or equivalent), and the initial mass of the lotion aliquot is determined to at least the nearest 0.001 g. Immediately following weighing, the weighing boat containing the lotion is placed in an oven held at 100° C. for 12±1 hour, at which point the boat containing the unevaporated material remaining from the aliquot is removed, and the mass of unevaporated material is determined to the nearest 0.001 g. The quotient of the unevaporated mass remaining from the lotion aliquot to the initial mass of the lotion aliquot, expressed as a percent to the nearest tenth of a percent, is defined as the Lotion Percent Solids Parameter. The Lotion Percent Solids Parameter is subtracted from 100.0%, and the resulting difference is defined as the Lotion Percent Water Parameter.

Buffering Capacity Test Method

In the Buffering Capacity Test Method, the mass of base solution required to bring a specified mass of lotion to a characteristic equivalence point is measured and expressed as a ratio of mass of added base to initial mass of lotion, and this dimensionless ratio is defined as the Equivalence Value.

The Lotion Expression Method is used to express 40.0±0.1 g of lotion. The pH of the lotion is measured to the nearest 0.01 unit of pH with a pH meter. If the pH of the lotion is equal to or greater than 10.00, the Equivalence Value is defined as 0. Otherwise, 0.1 N sodium hydroxide is added to the initial 40.0±0.1 g of expressed lotion with stirring and pH is measured and recorded as a function of added volume of base to the nearest 0.01 until the pH reaches 10.00. The pH versus mass 0.1 N sodium hydroxide added data are then examined, and the mass of added base at which the rate of change of pH with respect to addition of base is at a maximum is found and recorded in grams to the nearest 0.01 g as the Equivalence Mass. The Equivalence Mass divided by the initial mass of expressed lotion (40.0±0.1 g), then multiplied by 100, is defined as the Equivalence Value, reported to the hundredths place in dimensionless units.

Substrate Cellulosic Fiber Content Test Method

The content of cellulosic fibers (e.g. cotton, viscose rayon) of the wet wipe substrate is determined using common methods known to those of skill in the art to both identify the identity of fibers present and to choose an appropriate method for relative quantification. For example, ISO 1833-1977 can be used to quantify a variety of common mixtures of fibers, and in particular, section 10, Mixtures of Cellulose and Polyester Fibres, can be used to determine the content of cellulosic fibers in the presence of polyester fibers.

Organic Acid Content Test Methods

The weight percent of organic acid and the corresponding deprotonated conjugate base in the wet wipe lotion composition is determined using typical chemical analytical methods known to those skilled in the art. One example of determining the content of benzoic acid and conjugate base benzoate ion via High Pressure Liquid Chromatography (HPLC) is as follows.

In this method, HPLC performed using a mobile phase at a pH of approximately 2 is used to determine the content of total benzoate species of expressed wet wipe lotion. Here, total benzoate species refers to the presence of both benzoic acid and its conjugate base benzoate ion. The use of a mobile phase with a pH (pH approx. 2) significantly below the pKa of benzoic acid (pKa=4.2) results in essentially all benzoate species being in the form of benzoic acid, which is directly measured via HPLC separation and detection. The HPLC result can then be used together with the measured pH of expressed lotion to calculate the content of benzoic acid in the expressed lotion.

An HPLC instrument (such as Waters 2695, Waters Corporation, Milford, Mass., USA, or equivalent) is configured for isocratic separation with a flow rate of 1.5 mL/min, an injection volume of 10 μL, a column temperature of 35±1° C., and UV detection at a wavelength of 254 nm. An octadecyl reversed-phase silica column, 4.6×100 mm, particle size 3 or 3.5 μm, (such as Waters SunFire C18, part number #186002553, or equivalent) is used. A guard column (such as Phenomenex SecurityGuard Cartridges C18 4×2 mm, part number #AJO-4286, Phenomenex Inc., Torrence, Calif., USA, or equivalent) is recommended.

A phosphoric acid buffer mobile phase solution is prepared by adding 3.8±0.1 g of monosodium phosphate and 3.2±0.1 g of 85-90% phosphoric acid to 1300 mL of HPLC grade water and 325 mL of acetonitrile. Five standard solutions of benzoic acid are prepared using the mobile phase solution using class A volumetric pipettes and flasks with levels (precisely known) of approximately 20, 40, 100, 200, and 300 μg/mL.

The Lotion Expression Method is used to express all lotion from one package of wipes. (If this lotion is less than 50 mL in volume, the Lotion Expression Method is used to express lotion from additional like packages of wipes until the volume of expressed lotion exceeds 50 mL.) The pH of the quantity of lotion expressed is measured and recorded to the nearest 0.01 unit of pH. From the quantity of lotion expressed is weighed a sample 5.0±0.1 g (mass recorded to the nearest 0.1 mg), which is added to a 50 mL volumetric flask and diluted to volume with mobile phase. The ratio of sample mass to dilution volume, expressed in units of μg/mL, is defined as the dilution factor. This resulting solution is referred to as the sample as prepared. (If, after injection of standards and sample as prepared, it is found that the benzoic acid content of the sample as prepared lies outside the range of standards, another sample is prepared as above but adjusting the dilution such that the benzoic acid content lies within the range of benzoic acid standards, and a revised dilution factor is recorded.)

All five standards and the prepared sample are injected sequentially into the HPLC instrument. (Given the separation conditions specified, the benzoic acid peak generally occurs at around 5.5 minutes of elution time, but its exact position is confirmed via position in the standards.) A calibration curve of benzoic acid peak area versus benzoic acid concentration is fitted linearly to the peak areas of the five standards, and this linear fit is used to calculate the concentration (in μg/mL) benzoic acid in the sample as prepared, and this value is recorded to the nearest 0.1 µg/mL. The concentration of benzoic acid in the sample as prepared is then multiplied 100% and divided by the dilution factor to arrive at the weight percent of total benzoate species in the expressed lotion.

The measured pH of the expressed lotion is then used to determine how much of total benzoate species exists as benzoic acid at the pH of the expressed lotion. The ratio of benzoic acid to benzoate ion is found by the following equation.

$$\text{ratio of benzoic acid to benzoate} = \frac{10^{-pH}}{10^{-pK_a}}$$

And from this ratio, the weight percent of benzoic acid in the expressed lotion is found by the following equation.

$$\text{weight \% benzoic acid in expressed lotion} = \frac{\text{weight \% total benzoate species in expressed lotion}}{\left(1 + \frac{1}{\text{ratio of benzoic acid to benzoate}}\right)}$$

Microbiological Susceptibility Test Method

The Microbiological Susceptibility Test Method is used to determine the MST Yeast & Mold Value. The Microbiological Susceptibility Test Method follows United States Pharmacopoeia (51) Antimicrobial Effectiveness Testing and specifically follows the procedures for yeast and mold challenge of Category 2 products. The inoculation procedure is modified for application to wetted wipes as follows.

For each sample prepared, an entire previously sealed, unopened package of wetted wipes is opened, and 10.0±1.0 g of wipes is removed from as closely as possible to the middle of the stack of wipes and is aseptically weighed into a sterile container. Wipes are cut, if needed, in order for the sample to meet the mass target. Inoculums of yeast (*Candida albicans*) and mold (*Aspergillus brasiliensis*) are mixed in a 1:1 ratio to form a mixed inoculum. Prior to inoculation, the mixed yeast and mold inoculum is further diluted from the recommended level 1:10 in sterile 0.85% NaCl (w/w) saline solution. 1.0±0.1 mL of this resulting diluted inoculum is then spread as uniformly as is feasible across the wipes sample. Inoculated samples are stored at 22.5±2.5° C. until sampling. At the time of sampling, each wipes sample is added to 90 mL of liquid growth medium and is homogenized for two minutes at 260 RPM using a stomacher (such as the Stomacher 400 Circulator, Seward Ltd., West Sussex, UK, or equivalent). Additional 1:10 dilutions are performed using liquid growth medium (to achieve 1:100, 1:1000 dilutions and so on) as needed to enable a meaningful plate count. Plate counts are performed on 100-mm diameter petri plates, and ideal CFU readings for plates are between 25 and 250 for yeast and between 8 and 80 for mold. For each microorganism, the lowest dilution factor that leads to a raw CFU reading that falls within the allowed range is ideally used to calculate CFU/mL of survivors.

Using the determined starting and surviving concentration of each microorganism, as determined by USP (51), further quantities are defined and calculated. The Starting Yeast and Mold Concentration is defined as the sum of starting concentrations (in CFU/mL) for each of the microorganisms of yeast and mold analyzed. The Pooled Yeast and Mold Concentration at 28 Days is defined as the sum of measured concentration (in CFU/mL) of survivors for each of the microorganisms of yeast and mold analyzed.

The ratios of pooled microorganism count at 28 days versus the starting pooled microorganism count are used to calculate the MST Yeast & Mold Value. The MST Yeast & Mold Value is defined as $$\text{MST Yeast \& Mold Value} = -\log_{10} \frac{\text{Pooled Yeast and Mold Concentration at 28 Days}}{\text{Starting Pooled Yeast and Mold Concentration}}$$

and is reported to the nearest tenth of a log unit.

Examples & Data

The following examples and comparative examples are provided to help illustrate the lotion described herein. The exemplified lotions may be prepared by conventional formulation and mixing techniques. It will be appreciated that other modifications of the lotions described herein within the skill of those in the formulation art may be undertaken. All parts, percentages, and ratios herein are by weight unless otherwise specified. Some components may come from suppliers as dilute solutions. The amount stated reflects the weight percent of the active material, unless otherwise specified.

Examples 1-10 in Tables 1 and 2 show exemplary and comparative lotion formulations.

TABLE 1

| Ingredient | Ex. 1 | Ex. 2 | Ex. 3 | Ex. 4 | Ex. 5 |
|---|---|---|---|---|---|
| Water | 99.018 | 98.931 | 99.038 | 98.527 | 98.834 |
| PEG-40 HCO | 0.16 | 0.16 | 0.16 | 0.20 | 0.16 |
| Sorbitan Caprylate | 0.16 | 0.16 | 0.16 | 0.20 | 0.16 |
| Trisodium Citrate Dihydrate | 0.290 | 0.203 | 0.203 | 0.320 | 0.141 |
| Sodium Benzoate | 0.18 | 0.18 | 0.18 | 0.20 | 0.22 |
| Disodium EDTA | 0.10 | 0.10 | 0.10 | 0.10 | 0.10 |
| Citric Acid Anhydrous | 0.092 | 0.266 | 0.159 | 0.450 | 0.385 |
| pH | 3.8 | 4.2 | 4.6 | 4.0 | 3.8 |

TABLE 2

| Ingredient | Ex. 6 | Ex. 7 | Ex. 8 | Ex. 9 | Ex. 10 |
|---|---|---|---|---|---|
| Water | 98.995 | 99.090 | 98.802 | 98.958 | 99.069 |
| PEG-40 HCO | 0.16 | 0.16 | 0.16 | 0.16 | 0.16 |
| Sorbitan Caprylate | 0.16 | 0.16 | 0.16 | 0.16 | 0.16 |
| Trisodium Citrate Dihydrate | 0.141 | 0.141 | 0.140 | 0.140 | 0.140 |
| Sodium Benzoate | 0.22 | 0.22 | 0.24 | 0.24 | 0.24 |
| Disodium EDTA | 0.10 | 0.10 | 0.10 | 0.10 | 0.10 |
| Citric Acid Anhydrous | 0.224 | 0.130 | 0.398 | 0.242 | 0.132 |
| pH | 4.2 | 4.6 | 3.8 | 4.2 | 4.6 |

Examples 1-10 were made by the following formulation steps, all of which were performed at a temperature of 20-25° C.:

1. Create a 1:1 premix of PEG 40 hydrogenated castor oil and sorbitan caprylate, mixing with an IKA ULTRA-TURRAX® (for example model T-50 with a S 50 N-W 80 SMK jet mixer head) or equivalent mixer for 10 minutes at 5000-6000 rpm.

2. Add distilled, deionized water to the mixing vessel and start the mixing with the same mixer and speed as in step 1, maintaining this mixing throughout the entire process.
3. Add trisodium citrate dihydrate, mix 15 seconds, add sodium benzoate, mix 1 minute, add disodium EDTA, mix 1 minute.
4. Add PEG 40 hydrogenated castor oil and sorbitan caprylate premix slowly to the mixing vessel, taking 15-20 seconds to add and allow for incorporation. Mix for 2 minutes.
5. Add citric acid anhydrous.
6. Optionally add odor reduction composition.
7. Mix for 10 minutes.
8. Stop mixing. Confirm final pH is within desired range, e.g. target pH +/−0.1.

Table 3 shows MST Yeast & Mold Value measurements obtained from Examples 1-10 in Tables 1 and 2. The MST Yeast & Mold Value measurements were taken using the Microbiological Susceptibility Test Method provided herein. The higher the MST Yeast & Mold Value, the greater the preservation robustness of the wet wipe against yeast and mold growth.

TABLE 3

| Example | % Benzoic Acid in Lotion | % Sodium Benzoate in Lotion | MST Yeast & Mold Value Day 14 | MST Yeast & Mold Value Day 28 |
| --- | --- | --- | --- | --- |
| 1 | 0.061 | 0.024 | 3.5 | 4.2 |
| 2 | 0.053 | 0.053 | 3.3 | 3.7 |
| 3 | 0.038 | 0.093 | 2.0 | 2.7 |
| 4 | 0.066 | 0.041 | 3.8 | 4.0 |
| 5 | 0.077 | 0.030 | 4.5 | 4.5 |
| 6 | 0.067 | 0.066 | 4.2 | 4.2 |
| 7 | 0.047 | 0.118 | 2.3 | 2.6 |
| 8 | 0.084 | 0.033 | 4.5 | 4.5 |
| 9 | 0.072 | 0.072 | 4.2 | 4.5 |
| 10 | 0.053 | 0.131 | 2.3 | 3.4 |

The wet wipes described herein may have an MST Yeast & Mold Value at day 28 of from about 3 to about 5, alternatively from about 3.4 to about 4.8, alternatively from about 3.8 to about 5, alternatively from about 3.9 to about 4.7, and alternatively from about 4 to about 4.5, according to the Microbiological Susceptibility Test Method provided herein. The wet wipes described herein may have an MST Yeast & Mold Value at day 14 of from about 2.3 to about 5, alternatively from about 3 to about 5, alternatively from about 3.4 to about 4.8, alternatively from about 3.5 to about 4.5, alternatively from 4.2 to about 4.7, and alternatively from about 4 to about 4.5, according to the Microbiological Susceptibility Test Method provided herein.

Examples 11-15 in Table 4 show additional examples of lotion formulations as described herein.

TABLE 4

| Ingredient | Ex. 11 | Ex. 12 | Ex. 13 | Ex. 14 | Ex. 15 |
| --- | --- | --- | --- | --- | --- |
| Water | 99.018 | 98.527 | 98.834 | 98.995 | 98.722 |
| PEG-40 HCO | 0.16 | 0.20 | 0.16 | 0.16 | 0 |
| Glyceryl Caprylate | 0.16 | 0.20 | 0.16 | 0.16 | 0 |
| Trisodium Citrate Dihydrate | 0.290 | 0.320 | 0.141 | 0.141 | 0.140 |
| Sodium Benzoate, Sodium Gluconate, Sodium Levulinate, Sodium Anisate or mixtures thereof | 0.18 | 0.20 | 0.22 | 0.22 | 0.640 |
| Disodium EDTA or Sodium Gluconate | 0.10 | 0.10 | 0.10 | 0.10 | 0.10 |
| Citric Acid Anhydrous | 0.092 | 0.450 | 0.385 | 0.224 | 0.398 |
| pH | 3.8 | 4.0 | 3.8 | 4.2 | 3.8 |

Additional Examples/Combinations

A. An array of wet wipe packages displayed via a merchandise display system, the array of wet wipe packages comprising:
a) a first package comprising a first wet wipe, wherein the first wet wipe comprises a first coform nonwoven material and a first lotion, and wherein the first lotion is devoid of perfume;
b) a second package comprising a second wet wipe, wherein the second wet wipe comprises a second coform nonwoven material and a second lotion, wherein the second lotion comprises a perfume; and
c) a third package comprising a third wet wipe, wherein the third wet wipe comprises a third coform nonwoven material and a third lotion, wherein the third lotion is different than the first lotion and the second lotion;
wherein the first coform nonwoven material, the second coform nonwoven material, and/or the third coform nonwoven material comprise from about 14.5% to about 45% cotton by weight of the first coform nonwoven material, the second coform nonwoven material, and/or the third coform nonwoven material; and
wherein the first coform nonwoven material, the second coform nonwoven material, and/or the third coform nonwoven material comprise a matrix of a synthetic fiber, cellulosic fiber, and cotton fiber.
B. The array of wet wipe packages according to paragraph A, wherein at least one of the first lotion, the second lotion, and/or the third lotion has an Equivalence Value from about 30 to about 95.
C. The array of wet wipe packages according to paragraph A or B, wherein at least one of the first wet wipe, the second wet wipe, and the third wet wipe has an MST Yeast & Mold Value at day 28 from about 3 to about 5.
D. The array of wet wipe packages according to any of paragraphs A-C, wherein the cotton fiber is devoid of chlorine.
E. The array of wet wipe packages according to any of paragraphs A-D, wherein the first package comprises one or more communications that the first coform nonwoven material comprises cotton fibers and/or is devoid of chlorine.
F. The array of wet wipe packages according to any of paragraphs A-E, wherein the first package comprises one or more communications that the first lotion is devoid of fragrance and/or perfume.
G. The array of wet wipe packages according to any of paragraphs A-F, wherein the first lotion, the second lotion, and/or the third lotion comprise from about 98.5% to about 99.5% water by weight of the first lotion, the second lotion, and/or the third lotion, and wherein the first package, the second package, and/or the third package comprise one or more communications that the first lotion, the second lotion, and/or the third lotion comprise 99% water.

H. The array of wet wipe packages according to any of paragraphs A-G, wherein the first package, the second package, and/or the third package comprise a seal of cotton trademarked logo.

I. The array of wet wipe packages according to any of paragraphs A-H, wherein the cellulosic fiber is pulp fiber.

J. An array of wet wipe packages displayed via a merchandise display system, the array comprising:
  a) a first package comprising a first wet wipe, wherein the first wet wipe comprises a first coform nonwoven material and a first lotion, wherein the first lotion comprises aloe barbadensis leaf juice and tocopheryl acetate, and wherein the first lotion is devoid of fragrance and/or perfume;
  b) a second package comprising a second wet wipe, wherein the second wet wipe comprises a second coform nonwoven material and a second lotion, wherein the second lotion comprises *Cucumis sativus* fruit extract, glycerin, and a perfume;
  c) a third package comprising a third wet wipe, wherein the third wet wipe comprises a third coform nonwoven material and a third lotion, wherein the third lotion comprises coco-betaine, and wherein the third lotion is devoid of glycerin; and
  d) a fourth package comprising a fourth wet wipe, wherein the fourth wet wipe comprises a fourth coform nonwoven material and a fourth lotion, wherein the fourth coform nonwoven material comprises from about 14.5% to about 45% cotton by weight of the fourth conform nonwoven material, wherein the fourth lotion comprises from about 98.5% to about 99.5% water by weight of the fourth lotion, and wherein the fourth lotion is devoid of fragrance and/or perfume.

K. The array of wet wipe packages according to paragraph J, wherein the fourth lotion has an Equivalence Value from about 30 to about 95.

L. The array of wet wipe packages according to paragraph J or K, wherein the fourth lotion comprises from about 0.1% to about 0.5% sodium benzoate by weight of the fourth lotion.

M. The array of wet wipe packages according to any of paragraphs J-L, wherein the fourth lotion has a pH from about 3.8 to about 4.2.

N. The array of wet wipe packages according to any of paragraphs J-M, wherein the cotton is devoid of chlorine.

O. The array of wet wipe packages according to paragraph N, wherein the fourth package comprises one or more communications that the fourth coform nonwoven material comprises cotton fibers and/or is devoid of chlorine.

P. The array of wet wipe packages according to any of paragraphs J-O, wherein the fourth package comprises one or more communications that the fourth lotion is devoid of fragrance and/or perfume.

Q. The array of wet wipe packages according to any of paragraphs J-P, wherein the fourth package comprises one or more communications that the fourth lotion comprises 99% water.

R. The array of wet wipe packages according to any of paragraphs J-Q, wherein the fourth package comprises a seal of cotton trademarked logo.

S. An array of wet wipe packages displayed via a merchandise display system, the array comprising:
  a) a first package comprising a first wet wipe, wherein the first wet wipe comprises a first coform nonwoven material and a first lotion, wherein the first coform nonwoven material comprises from about 14.5% to about 45% cotton by weight of the first coform nonwoven material, wherein the first lotion comprises aloe barbadensis leaf juice, tocopheryl acetate, and from about 98.5% to about 99.5% water by weight of the first lotion, wherein the first lotion is devoid of fragrance and/or perfume, wherein the first package comprises one or more communications that the first coform nonwoven material comprises cotton, and wherein the first package comprises one or more communications that the first lotion comprises 99% water;
  b) a second package comprising a second wet wipe, wherein the second wet wipe comprises a second coform nonwoven material and a second lotion, wherein the second lotion comprises *Cucumis sativus* fruit extract, glycerin, and a perfume; and
  c) a third package comprising a third wet wipe, wherein the third wet wipe comprises a third coform nonwoven material and a third lotion, wherein the third lotion comprises coco-betaine, and wherein the third lotion is devoid of glycerin.

T. The array of wet wipe packages according to paragraph S, wherein the first lotion has an Equivalence Value from about 30 to about 95.

U. The array of wet wipe packages according to paragraph S or T, wherein the first package comprises a seal of cotton trademarked logo.

V. The array of wet wipe packages according to any of paragraphs S-U, wherein the first package comprises one or more communications that the first coform nonwoven material is devoid of chlorine and/or is devoid of phthalate.

W. The array of wet wipe packages according to any of paragraphs S-V, wherein the first package comprises one or more communications that the first lotion is devoid of fragrance and/or perfume.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. An array of wet wipe packages displayed via a merchandise display system, the array of wet wipe packages comprising:
   a first package comprising a first wet wipe, wherein the first wet wipe comprises a first coform nonwoven material and a first lotion;
   a second package comprising a second wet wipe, wherein the second wet wipe comprises a second coform nonwoven material and a second lotion; and
   a third package comprising a third wet wipe, wherein the third wet wipe comprises a third coform nonwoven material and a third lotion, and wherein the third lotion is different than the first lotion and/or the second lotion;
   wherein the first coform nonwoven material, the second coform nonwoven material, and/or the third coform nonwoven material comprise from about 14.5% to about 45% cotton by weight of the first coform nonwoven material, the second coform nonwoven material, and/or the third coform nonwoven material;
   wherein the first lotion comprises from about 0.061% to 0.084% by weight benzoic acid, from 0.024% to 0.072% by weight of sodium benzoate, and where the amount of benzoic acid is greater than or equal to the amount of sodium benzoate; where the lotion has pH about 3.6 to about 4.2; and
   wherein the first coform nonwoven material, the second coform nonwoven material, and/or the third coform nonwoven material comprise a matrix of synthetic fibers, cellulosic fibers, and cotton fibers.

2. The array of wet wipe packages of claim 1, wherein at least one of the first lotion, the second lotion, and/or the third lotion has an Equivalence Value from about 30 to about 95, according to the Buffering Capacity Test Method.

3. The array of wet wipe packages of claim 1, wherein at least one of the first wet wipe, the second wet wipe, and the third wet wipe has an MST Yeast & Mold Value at day 28 from about 3 to about 5, according to the Microbiological Susceptibility Test Method.

4. The array of wet wipe packages of claim 1, wherein the cotton fibers are devoid of chlorine.

5. The array of wet wipe packages of claim 1, wherein the first lotion is devoid of fragrance and/or perfume.

6. The array of wet wipe packages of claim 1, wherein the second lotion is devoid of fragrance and/or perfume.

7. The array of wet wipe packages of claim 1, wherein the first lotion, the second lotion, and/or the third lotion comprise from about 98% to about 99.9% water by weight of the first lotion, the second lotion.

8. The array of wet wipe packages of claim 1, wherein the first package, the second package, and/or the third package comprise a seal of cotton trademarked logo.

9. The array of wet wipe packages of claim 1, wherein the cellulosic fibers are pulp fiber.

10. An array of wet wipe packages displayed via a merchandise display system, the array of wet wipe packages comprising:
    a first package comprising a first wet wipe, wherein the first wet wipe comprises a first nonwoven material and a first lotion;
    a second package comprising a second wet wipe, wherein the second wet wipe comprises a second nonwoven material and a second lotion; and
    a third package comprising a third wet wipe, wherein the third wet wipe comprises a third nonwoven material and a third lotion, and wherein the third lotion is different than the first lotion and/or the second lotion;
    wherein the first nonwoven material, the second nonwoven material, and/or the third nonwoven material comprise from about 14.5% to about 100% cotton by weight of the first nonwoven material, the second nonwoven material, and/or the third nonwoven material; and
    wherein the first lotion comprises from about 0.061% to 0.084% by weight benzoic acid, from 0.024% to 0.072% by weight of sodium benzoate, and where the amount of benzoic acid is greater than or equal to the amount of sodium benzoate; where the lotion has pH about 3.6 to about 4.2.

11. The array of wet wipe packages of claim 10, wherein the first lotion is devoid of fragrance and/or perfume.

12. The array of wet wipe packages of claim 10, wherein the second lotion is devoid of fragrance and/or perfume.

13. The array of wet wipe packages of claim 10, wherein the second nonwoven material comprises between about 5% and about 85% lyocell by weight of the second nonwoven material.

14. The array of wet wipe packages of claim 10, wherein the third nonwoven material comprises between about 5% and about 50% viscose by weight of the third nonwoven material.

15. The array of wet wipe packages of claim 10, wherein the second nonwoven material and/or the third nonwoven material comprises between about 5% and about 85% natural cellulosic fibers by weight of the second nonwoven material and/or the third nonwoven material.

16. The array of wet wipe packages of claim 10, wherein the natural cellulosic fibers are wood pulp fibers.

17. An array of wet wipe packages displayed via a merchandise display system, the array of wet wipe packages comprising:
    a first package comprising a first wet wipe, wherein the first wet wipe comprises a first nonwoven material and a first lotion, and wherein the first nonwoven material comprises from about 5% to about 85% cotton by weight of the first nonwoven material;
    a second package comprising a second wet wipe, wherein the second wet wipe comprises a second nonwoven material and a second lotion, and wherein the second nonwoven material comprises from about 5% to about 50% natural fibers; and
    a third package comprising a third wet wipe, wherein the third wet wipe comprises a third nonwoven material and a third lotion, and wherein the third nonwoven material comprises between about 5% and about 85% natural cellulosic fibers by weight of the third nonwoven material;
    wherein the first lotion comprises from about 0.061% to 0.084% by weight benzoic acid, from 0.024% to 0.072% by weight of sodium benzoate, and where the amount of benzoic acid is greater than or equal to the amount of sodium benzoate; where the lotion has pH about 3.6 to about 4.2.

18. The array of wet wipe packages of claim 17, wherein the second nonwoven material comprises viscose and/or lyocell.

19. The array of wet wipe packages of claim 17, wherein the second nonwoven material further comprises cotton.

20. The array of wet wipe packages of claim 17, wherein the natural cellulosic fibers comprise wood pulp.

* * * * *